United States Patent [19]

Ungarelli et al.

[11] Patent Number: 4,675,462

[45] Date of Patent: Jun. 23, 1987

[54] PROCESS FOR THE PREPARATION OF (2,2)-PARACYCLOPHANE

[75] Inventors: Raffaele Ungarelli, Trecate; Maurizio A. Beretta, Milan; Loris Sogli, Novara, all of Italy

[73] Assignee: Montedison S.p.A., Milan, Italy

[21] Appl. No.: 924,274

[22] Filed: Oct. 29, 1986

[30] Foreign Application Priority Data

Oct. 30, 1985 [IT] Italy ............................. 22667 A/85

[51] Int. Cl.$^4$ ............................................. C07C 2/72
[52] U.S. Cl. .................................. 585/429; 585/359; 585/426; 585/427; 585/428
[58] Field of Search ............... 585/426, 427, 428, 429, 585/359

[56] References Cited

U.S. PATENT DOCUMENTS 3,247,274  4/1966  Pollart ................................. 585/428
3,258,504  6/1966  Lenaers .............................. 585/428
3,754,015  8/1973  Hedaya .............................. 585/426
4,359,327  11/1982 Armand et al. .................... 585/426
4,532,369  7/1985  Hartner ............................. 585/428

OTHER PUBLICATIONS

Neuschwander et al., J. Chemistry, vol. 20, 288–290 (1980).
Gray et al., J. Am. Chem. Soc., vol. 101, (8), 2128–36 (1979).

Primary Examiner—Asok Pal
Attorney, Agent, or Firm—Stevens, Davis, Miller & Mosher

[57] ABSTRACT

A process for the preparation of (2,2)-paracyclophane by conversion of p.methylbenzyltrimethylammonium halide to the corresponding hydroxide and by Hofmann elimination from p.methylbenzyltrimethylammonium hydroxide, wherein both reactions are carried out in the same aqueous solution of an alkaline hydroxide and in the presence of a copper or iron compound.

10 Claims, No Drawings

PROCESS FOR THE PREPARATION OF (2,2)-PARACYCLOPHANE

The invention relates to a process for preparing (2,2)paracyclophane having formula:

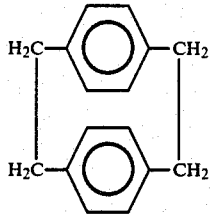

(I)

More particularly, the invention provides a process for preparing (2,2)-paracyclophane having formula (I) starting from a p.methylbenzyltrimethylammonium halide having formula:

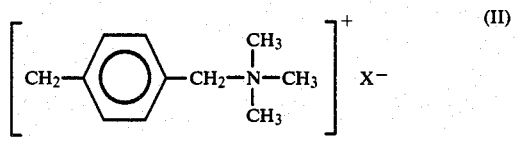

(II)

in which X is a halogen such as chlorine, bromine, etc., by conversion to the corresponding hydroxide and Hofmann elimination of the obtained hydroxide.

BACKGROUND OF THE INVENTION (2,2)-paracyclophane is a well-known product and it is mainly utilized in the preparation of poly-p.xylylene, a high-performance product because of its capability of coating surfaces.

Various processes have been suggested for preparing (2,2)-paracyclophane (I). Such known processes, however, are not fully satisfactory and are not suitable for industrial use, owing to the low yield of the process and to the difficult recovery of the product from the reaction mixture.

Thus, for example, "Organic Syntheses", Coll. Vol. 5, John Wiley & Sons, Inc., New York/London/Sydney/Toronto, 1973, pages 883–886, describes a process for preparing (2,2)-paracyclophane by Hofmann elimination from p.methylbenzyltrimethylammonium hydroxide obtained by reaction of the corresponding bromide with silver oxide. The elimination was carried out in the presence of an inert organic solvent (toluene) and a yield of 10–11% was obtained, with formation of undesired polymeric by-products difficult to separate.

According to European patent application No. 108,297, corresponding to U.S. Pat. No. 4,532,369, the reaction yield can be raised if Hofmann elimination occurs in the presence of high amounts of dimethylsulfoxide. This process permits to obtain high yields (about 70%), but the dimethylsulfoxide recovery makes the process relatively little attractive for industrial applications. Furthermore, the (2,2)-paracyclophane prepared by this process is not fully satisfactory as regards its purity degree.

Generally, in all the known processes for preparing (2,2)-paracyclophane, considerable amounts of poly-p.xylylene are formed, which, in the presence of the organic solvent in the reaction medium, assumes a gelatine-like appearance and is not readily separable by filtration. To overcome this drawback it would be advisable to conduct the Hofmann elimination reaction in the absence of any organic solvents. However, from British Pat. No. 807,196 it is known that p.methylbenzyltrimethylammonium hydroxide, when treated at temperatures higher than 100° C. in an aqueous solution of an alkaline hydroxide, essentially generates poly-p.xylylene.

THE PRESENT INVENTION

An object of the present invention is to provide pure (2,2)-paracyclophane with industrially acceptable yields by carrying out the reaction in an aqueous phase, in the absence of organic solvents, so as to achieve a considerable increase in yields and to obtain a polymeric by-product which can be readily separated by filtration.

We have now found that this and still further objects are achieved by carrying out both the conversion of p.methylbenzyltrimethylammonium halide of formula (II) to the corresponding hydroxide and the Hofmann elimination from the latter, in an aqueous phase consisting of a solution of an alkaline hydroxide having a concentration higher than 20% by weight, and in the presence of at least a catalytic amount of a copper or an iron compound.

Any organic or inorganic copper or iron compound may be utilized in the process of the present invention, such as, e.g., a salt, an oxide or a hydroxide. In particular, the salts of copper (II) and of iron (III) are preferred.

Examples of useful salts are cupric or ferric chloride, cupric or ferric nitrate, cupric or ferric sulphate, cupric or ferric acetate, etc.; best results were obtained by using cupric or ferric chloride.

In the process according to the invention, the catalytic action exerted by the copper or iron compounds is particularly surprising when considering that the corresponding metal compounds having an analogous chemical behavior, such as the compounds of chrome, nickel or titanium, have either no effect or a negative effect under the same reaction conditions.

The concentration of the copper compound or of the iron compound in the reaction medium is not critical, provided its amount is at least the catalytic amount. Generally, amounts from 0.1% to 10% by moles, referred to p.methylbenzyltrimethylammonium halide, can be used.

According to the invention, the process is carried out in aqueous phase in the absence of any organic solvents. The aqueous phase consists of an alkaline hydroxide solution having a concentration higher than 20% by weight. Preferred alkaline hydroxides are sodium hydroxide and potassium hydroxide. The concentration of the aqueous solution is preferably maintained, during Hofmann elimination reaction, at from 30 to 40% by weight.

In the process of the invention, Hofmann elimination from p.-methylbenzyltrimethylammonium hydroxide, formed in situ by reacting the corresponding halide with the alkaline hydroxide, can be conducted at a temperature from 50° to 150° C., preferably from 100° to 130° C., and for a time from 1 to 50 hours and preferably from 2 to 10 hours.

At the end of the elimination reaction, the resultant product is separated by means of known and substantially conventional techniques.

The process of the present invention permits to obtain, with industrially acceptable yields, (2,2)-paracyclophane with a high degree of purity (higher than 99.5%) and a high productivity, thanks to the reduction of the reaction volume and to the increase in the filtration rate of the polymeric slurry.

The present invention is further clarified by the following examples, which are given for merely illustrative purposes and are not to be construed as being limitative of the invention.

In these examples, all parts, percentages and ratios are by weight, unless otherwise indicated.

EXAMPLE 1 (Comparative Test)

Into a 1,000 ml flask equipped with a stirrer, a thermometer and a condenser, there were charged:

100 g of an aqueous solution containing 40% by weight of NaOH (1 mole), and 62.5 g of an aqueous solution at 63.9% by weight of p-methylbenzyltrimethylammonium chloride (0.2 moles).

Under continuous stirring, the solution was heated by gradually raising the temperature from 22° C. to 120° C. The NaOH concentration was maintained at 35% by weight. The solution was maintained at the boiling temperature for 5 hours.

The resulting (2,2)-paracyclophane was separated from the reaction mass by solubilization in 300 ml of xylene. To this purpose, xylene was added to the reaction mass and the slurry was maintained at total reflux under stirring for 0.5 hour. It was filtered at 95° C., the aqueous phase was separated from the organic solution which was repeatedly washed with water and concentrated to small volume. The xylene solution was cooled down to 20° C., and the precipitated solid product was recovered by filtration. After washing of the solid product with acetone and after drying, there were obtained 1.08 g of a white crystalline solid product having a melting point of 283-285° C. and resulting, by gas-chromatographic analysis, to be (2,2)-paracyclophane with a purity of about 99.5%.

EXAMPLES 2–8

Example 1 was repeated, adding to the aqueous NaOH solution a compound of the type and in the amount indicated in the following Table I. The amount of (2,2)-paracyclophane obtained, its melting point as well as the reaction yield are also reported in Table I.

TABLE I

| Added salt | | Product obtained | | | |
|---|---|---|---|---|---|
| Type | Amount in g | Grams | Yield in % mole | Purity % | Melting point °C. |
| — | — | 1.08 | 5.2 | 99.5 | 283–285 |
| $FeCl_3.6H_2O$ | 0.54 | 3.2 | 15.4 | 99.8 | 283–284 |
| $CuSO_4.5H_2O$ | 0.50 | 4.36 | 20.1 | 99.8 | 283–284 |
| $Cu(OOC-CH_3)_2.H_2O$ | 0.40 | 5.30 | 25.5 | 99.8 | 284–285 |
| $CuCl_2.2H_2O$ | 0.17 | 4.8 | 23.1 | 99.8 | 284–285 |
| $CuCl_2.2H_2O$ | 0.34 | 5.84 | 28.1 | 99.8 | 283–285 |
| $CuCl_2.2H_2O$ | 1.02 | 4.98 | 24. | 99.5 | 284–285 |
| $CuO$ | 0.16 | 5.40 | 26. | 99.8 | 283–285 |

What is claimed is:

1. A process for preparing (2,2)-paracyclophane starting from a p.methylbenzyltrimethylammonium halide, by conversion of said p.methylbenzyltrimethylammonium halide to the corresponding hydroxide and by Hofmann elimination from the latter, both reactions being carried out in an aqueous phase consisting of an alkaline hydroxide solution having a concentration higher than 20% by weight, characterized in that both reactions are conducted in the presence of at least a catalytic amount of a copper compound or of an iron compound.

2. The process of claim 1, wherein both reactions are carried out in the presence of a copper compound or of an iron compound selected from a salt, an oxide and a hydroxide.

3. The process of claim 1 wherein a salt of copper (II) or of iron (III) is used.

4. The process of claim 3, wherein the salt of copper (II) or of iron (III) is selected from: cupric chloride, ferric chloride, cupric nitrate, ferric nitrate, cupric sulphate, ferric solphate, cupric acetate and ferric acetate.

5. The process of claim 4, wherein the salt of copper (II) or of iron (III) is cupric chloride or ferric chloride.

6. The process of claim 1, wherein the amount of copper or of iron compound ranges from 0.1 to 10% by moles with respect to p.methylbenzyltrimethylammonium halide.

7. The process of claim 1, wherein the concentration of the aqueous solution of an alkaline hydroxide is maintained, during Hofmann elimination reaction, from 30 to 40% by weight.

8. The process of claim 1, wherein Hofmann elimination is carried out from p.methylbenzyltrimethylammonium hydroxide formed in situ by the reaction of the corresponding halide of formula (II) with alkaline hydroxide.

9. The process of claim 1, wherein Hofmann elimination is carried out at a temperature from 50° to 150° C., for a time of 1 to 50 hours.

10. The process of claim 1, wherein Hofmann elimination is carried out at a temperature from 100° C. to 130° C. and for a time of 2 to 10 hours.

* * * * *